(12) United States Patent
Levy et al.

(10) Patent No.: US 10,478,133 B2
(45) Date of Patent: Nov. 19, 2019

(54) SYSTEMS AND METHODS FOR CALIBRATING A NUCLEAR MEDICINE IMAGING SYSTEM

(71) Applicant: General Electric Company, Schenectady, NY (US)

(72) Inventors: Moshe Levy, Zichron Yakov (IL); Jean-Paul Bouhnik, Zichron Yakov (IL); Yariv Grobshtein, Haifa (IL); Gil Amisar, Haifa (IL); Yaron Hefetz, Kibbutz Alonim (IL)

(73) Assignee: General Electric Company, Schenectady, NY (US)

(*) Notice: Subject to any disclaimer, the term of this patent is extended or adjusted under 35 U.S.C. 154(b) by 188 days.

(21) Appl. No.: 15/298,940

(22) Filed: Oct. 20, 2016

(65) Prior Publication Data

US 2018/0110496 A1    Apr. 26, 2018

(51) Int. Cl.
*A61B 6/00* (2006.01)
*A61B 6/03* (2006.01)
*A61B 6/06* (2006.01)

(52) U.S. Cl.
CPC ............... *A61B 6/037* (2013.01); *A61B 6/06* (2013.01); *A61B 6/545* (2013.01); *A61B 6/585* (2013.01)

(58) Field of Classification Search
CPC .................................................. A61B 6/582
See application file for complete search history.

(56) References Cited

U.S. PATENT DOCUMENTS

| | | | | |
|---|---|---|---|---|
| 4,833,327 A | * | 5/1989 | Hart | G01T 1/2928 250/363.01 |
| 5,245,190 A | * | 9/1993 | Sibbald | G02B 26/04 250/233 |
| 5,757,006 A | * | 5/1998 | DeVito | G01T 1/1642 250/363.04 |
| 6,242,743 B1 | * | 6/2001 | DeVito | A61B 6/037 250/363.01 |

(Continued)

FOREIGN PATENT DOCUMENTS

WO    WO 2009122317 A2 * 10/2009 ............. A61B 6/032

OTHER PUBLICATIONS

Bailey, D. et al., "An Evidence-Based Review of Quantitative SPECT Imaging and Potential Clinical Applications," Journal of Nuclear Medicine, vol. 54, No. 1, Jan. 2013, 7 pages.

(Continued)

*Primary Examiner* — David P Porta
*Assistant Examiner* — Djura Malevic
(74) *Attorney, Agent, or Firm* — McCoy Russell LLP

(57) ABSTRACT

Methods and systems are provided for calibrating a nuclear medicine imaging system. In one embodiment, a method comprises: detecting, with a plurality of detectors, photons emitted by a calibration source comprising a radioactive line source and a fluorescence source, while pivoting one or more detectors of the plurality of detectors; and calibrating, with a processor communicatively coupled to the plurality of detectors, each detector of the plurality of detectors based on energy measurements of the detected photons. In this way, a two-point energy calibration of detectors can be performed with a single isotope, and without removing or adjusting a collimator attached to the detector.

20 Claims, 7 Drawing Sheets

(56) References Cited

U.S. PATENT DOCUMENTS

| | | | | |
|---|---|---|---|---|
| 6,652,441 B2* | 11/2003 | Weinberger | A61N 5/1002 | 600/3 |
| 7,118,729 B1* | 10/2006 | O'Foghludha | A61N 5/1001 | 424/1.11 |
| 7,127,029 B2* | 10/2006 | Francke | A61B 6/02 | 378/22 |
| 7,312,456 B2* | 12/2007 | Joung | G01T 1/1641 | 250/363.04 |
| 7,465,930 B2* | 12/2008 | Joung | G01T 1/1648 | 250/361 R |
| 7,705,316 B2* | 4/2010 | Rousso | G01T 1/161 | 250/370.09 |
| 8,094,894 B2* | 1/2012 | Nagler | A61B 6/00 | 382/128 |
| 8,098,795 B2* | 1/2012 | Nowak | G01T 1/00 | 378/62 |
| 8,194,237 B2* | 6/2012 | Cronin | H01L 27/14601 | 356/71 |
| 8,338,788 B2* | 12/2012 | Zilberstein | G01T 1/1611 | 250/363.04 |
| 8,384,015 B2* | 2/2013 | Blevis | G01T 1/1648 | 250/252.1 |
| 8,421,021 B2* | 4/2013 | Sachs | G06T 11/005 | 250/336.1 |
| 8,552,389 B2* | 10/2013 | Jansen | A61B 6/037 | 250/363.1 |
| 8,696,201 B2* | 4/2014 | Kraft | G01T 7/005 | 378/207 |
| 8,748,827 B2* | 6/2014 | Zilberstein | G01T 1/1611 | 250/363.04 |
| 8,876,377 B2 | 11/2014 | Silberklang et al. | | |
| 9,006,673 B2* | 4/2015 | Ito | G01T 1/17 | 250/370.09 |
| 9,072,441 B2* | 7/2015 | Shai | A61B 6/032 | |
| 9,297,913 B2* | 3/2016 | Grobshtein | G01T 1/1647 | |
| 9,439,607 B2* | 9/2016 | Khen | A61B 6/4258 | |
| 9,554,489 B2* | 1/2017 | Hefetz | H05K 7/20418 | |
| 9,606,247 B2* | 3/2017 | Kovalski | G01T 1/2985 | |
| 9,763,639 B2* | 9/2017 | Lee | A61B 6/032 | |
| 9,907,523 B2* | 3/2018 | Hofmann | H01L 27/14601 | |
| 10,278,657 B2* | 5/2019 | Peretz | A61B 6/037 | |
| 2004/0262525 A1* | 12/2004 | Yunker | G01T 1/1648 | 250/363.08 |
| 2007/0221853 A1* | 9/2007 | Joung | G01T 1/1642 | 250/363.09 |
| 2008/0011954 A1* | 1/2008 | Hefetz | G01T 1/1642 | 250/363.02 |
| 2008/0073539 A1* | 3/2008 | Vija | G01T 1/1611 | 250/363.04 |
| 2011/0147574 A1* | 6/2011 | Blevis | G01T 1/1648 | 250/252.1 |
| 2015/0065873 A1* | 3/2015 | Tsukerman | A61B 6/5205 | 600/436 |
| 2015/0276949 A1* | 10/2015 | Grobshtein | G01T 1/1647 | 250/362 |
| 2015/0342543 A1* | 12/2015 | Khen | G01T 1/161 | 250/362 |
| 2015/0371808 A1* | 12/2015 | Turyanskiy | H01J 35/18 | 378/140 |
| 2016/0077216 A1* | 3/2016 | Hefetz | H05K 7/20418 | 250/336.1 |
| 2017/0258412 A1* | 9/2017 | Daerr | A61B 6/032 | |

OTHER PUBLICATIONS

Naot, A., "Systems and Methods for Detector Sensitivity Calibration in Nuclear Medicine Imaging," U.S. Appl. No. 15/298,825, filed Oct. 20, 2016, 27 pages.

* cited by examiner

SYSTEMS AND METHODS FOR CALIBRATING A NUCLEAR MEDICINE IMAGING SYSTEM

FIELD

Embodiments of the subject matter disclosed herein relate to medical imaging systems, and more particularly, to calibrating a nuclear medicine (NM) imaging system.

BACKGROUND

In nuclear medicine imaging, systems with multiple detectors or detector heads may be used to image a subject. For example, the detectors may be positioned adjacent to the subject to acquire nuclear medicine imaging data (e.g., radioactivity), which is used to generate a three-dimensional (3D) image of the subject. In a specific example, Single Photon Emission Computed Tomography (SPECT) systems may have moving detector heads, such as gamma cameras, positioned to focus on a region of interest. One or more of the gamma cameras may be moved (for example, rotated) to different angular positions to acquire image data. The acquired image data may then be used to generate 3D images.

In single photon imaging systems, such as planar or SPECT imaging systems, collimators may be placed in front of a scintillation crystal or solid state detector to focus the field of view (FOV) of the detectors. The collimators allow gamma rays aligned with the holes of the collimators to pass through to the detector. These detectors need to be calibrated, including during manufacture and periodically after installation, to ensure proper imaging operation. For example, the detectors are calibrated to provide a uniform energy and sensitivity response across the detector units or output channels.

Calibration of these collimated detectors is performed using a calibration emission source that exposes the detectors, and more particularly the entire detector or array of detectors, to radioactive emissions. Accordingly, in pixelated detectors, each pixel is exposed to a statistically relevant number of photons. In some collimated detector systems, calibration with multiple isotopes (having different energy peaks) is not practical after the system is assembled. Accordingly, in collimated detectors, the calibration is performed on the detectors having the collimators removed and using a jig or guide. This enables a two point energy calibration (gain and offset), wherein the calibration uses at least two isotope sources with two different peaks for calibration. Such an approach is time-consuming and difficult, as the detectors must be disassembled and multiple calibrations must be performed.

BRIEF DESCRIPTION

In one embodiment, a method comprises: detecting, with a plurality of detectors, photons emitted by a calibration source comprising a radioactive line source and a fluorescence source, while pivoting one or more detectors of the plurality of detectors; and calibrating, with a processor communicatively coupled to the plurality of detectors, each detector of the plurality of detectors based on energy measurements of the detected photons. In this way, a two-point energy calibration of detectors can be performed with a single isotope, and without removing or adjusting a collimator attached to the detector.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
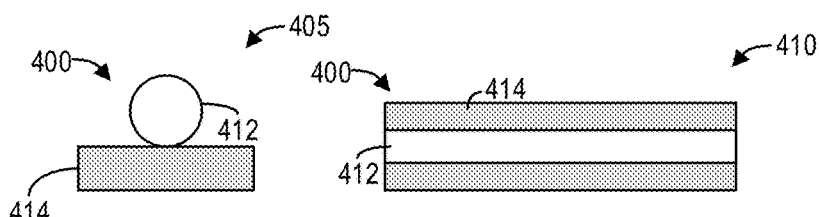
FIG. 4 shows multiple views of an example calibration source in accordance with an embodiment.
Figure 5:
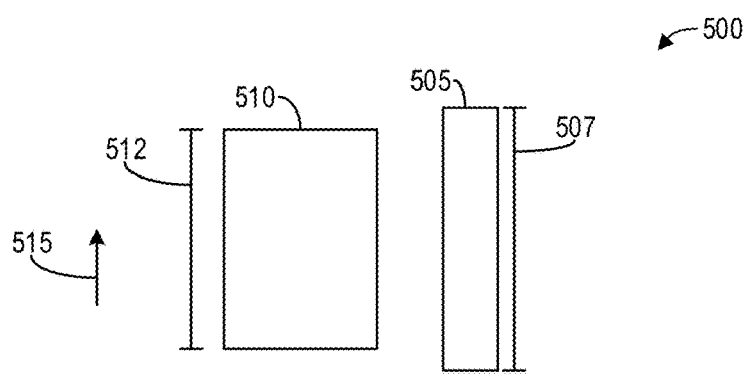
FIG. 5 shows a block diagram illustrating relative sizes of a detector and a calibration source in accordance with an embodiment.
Figure 6:
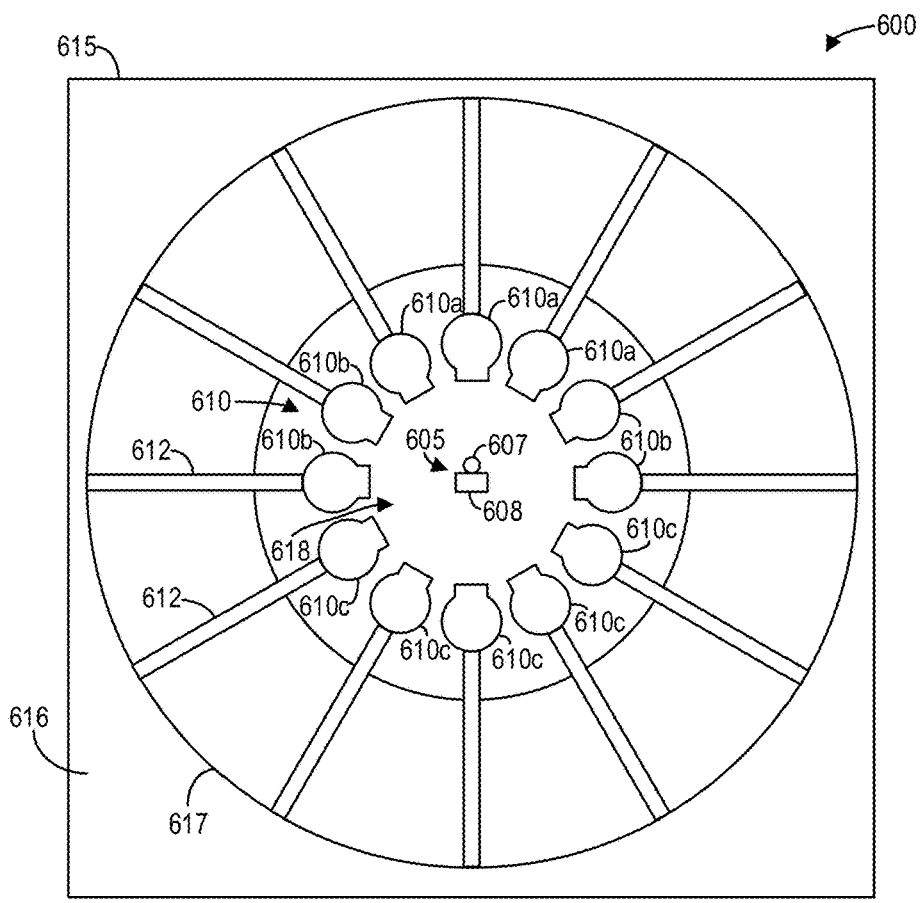
FIG. 6 shows a block diagram illustrating the example calibration source of FIG. 4 positioned within a NM imaging system in accordance with an embodiment.
Figure 7:
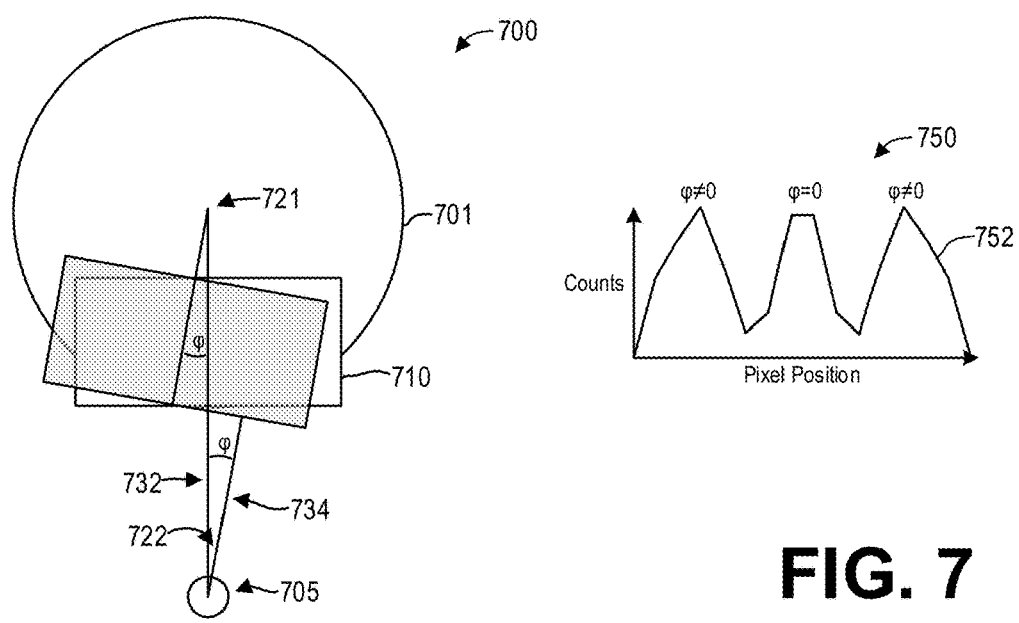
FIG. 7 shows a diagram illustrating geometry of a detector head while rotating in accordance with an embodiment.

The following description relates to various embodiments of nuclear medicine imaging systems. In particular, systems and methods are provided for a calibration source for a nuclear medicine (NM) imaging system that enables calibration of detectors of the NM imaging system at multiple energy peaks (e.g., two-peak energy calibration) using a single isotope. An imaging system, such as the imaging system depicted in FIG. 1, may include systems for controlling the movement of a plurality of imaging detectors to position the imaging detectors to acquire image data. For example, in various embodiments a Nuclear Medicine (NM) imaging system with an array of detector heads that are individually and independently movable is provided, as depicted in FIG. 2. In some embodiments, one or more of the heads are capable of a plurality of types of movement, such as rotation and linear motion. For example, the detector heads may be configured to be positioned adjacent or proximate to a subject and rotated, such as to increase the field of view of the detector heads. A calibration source for calibrating the energy and sensitivity response of the detector heads may have an energy spectrum, such as the energy spectrum shown in FIG. 3, with multiple energy peaks, such that the gain and offset of a detector head can be calibrated with a single calibration source. To that end, a calibration source may include a cylindrical line source in addition to an x-ray fluorescence source, as depicted in FIG. 4. To avoid repositioning the calibration source within the imaging system during calibration, the line source may be as least as long as the detector's field of view, as depicted in FIG. 5. The emission of radiation by the calibration source may be anisotropic within the imaging system, as depicted in FIG. 6. A detector head may be rotated or pivoted so that the calibration source is within the field-of-view of each pixel of the detector head; this pivoting may necessitate a geometric correction to acquired data, as depicted in FIG. 7. A method for calibrating a NM imaging system, such as the method depicted in FIG. 8, may include rotating the gantry of the imaging system if the calibration source is anisotropic. However, some calibration sources, such as the calibration sources depicted in FIGS. 9-13, are isotropic, and so no rotation of the gantry is necessary.

Figure 1:
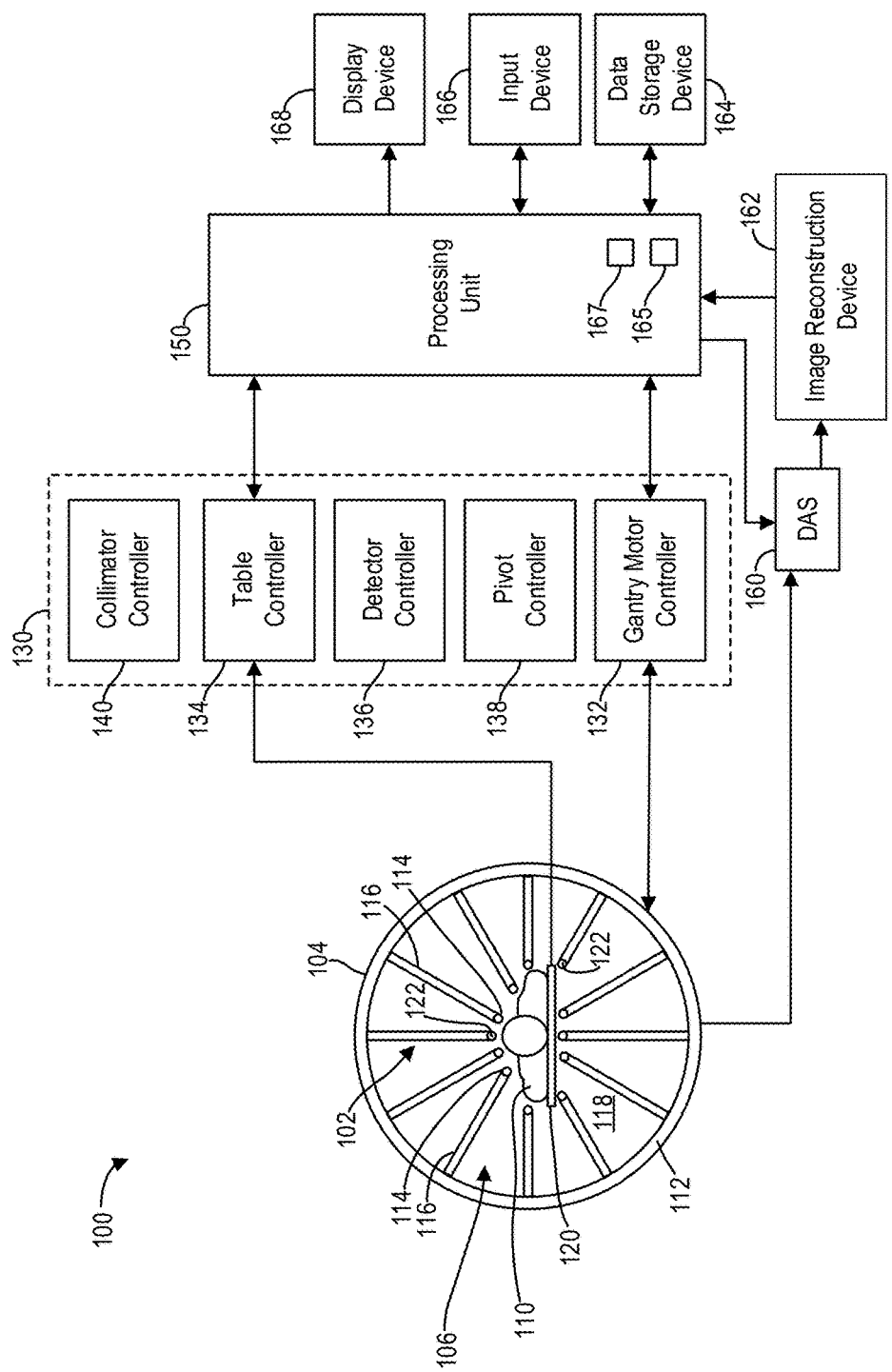
FIG. 1 is a schematic block diagram of a nuclear imaging (NM) imaging system in accordance with an embodiment.
Figure 2:
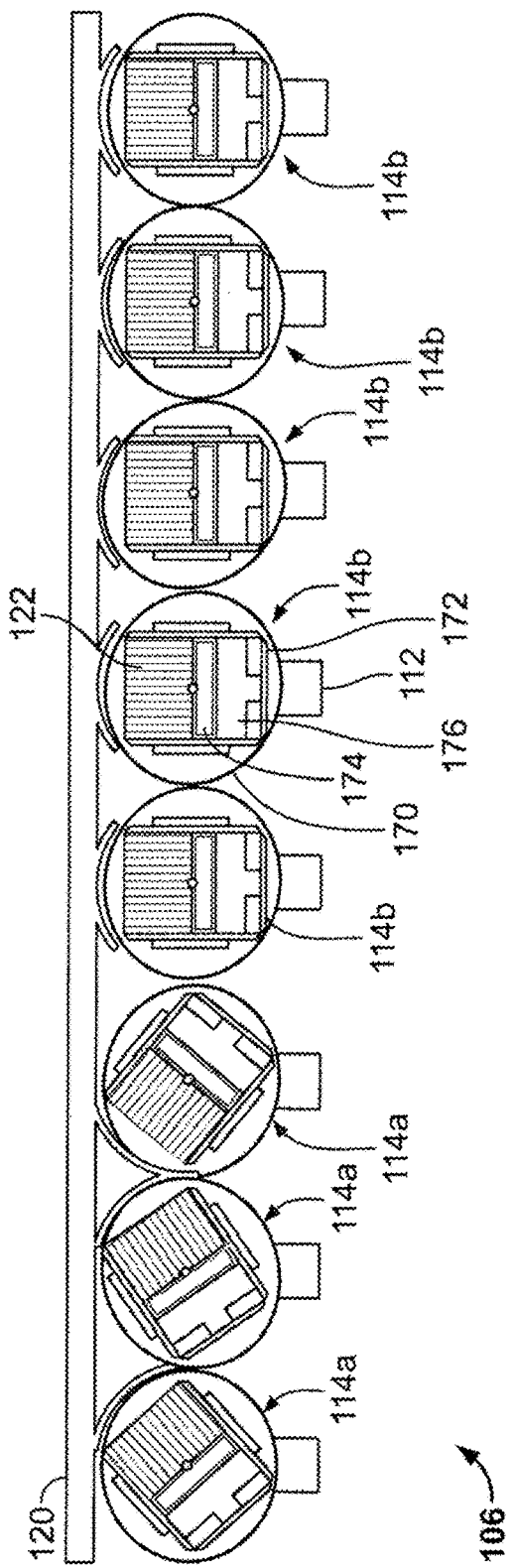
FIG. 2 is a schematic block diagram illustrating detector units in accordance with an embodiment.

FIG. 1 is a schematic illustration of a NM imaging system 100 having a plurality of imaging detectors mounted on a gantry. The imaging detectors may be configured to rotate around a fixed pivot. The movement of the imaging detectors is controlled to reduce the likelihood or avoid collision among the moving imaging detectors and/or reduce the likelihood of one imaging detector obstructing the field of view of another imaging detector. For example, the NM imaging system in some embodiments provides coordinated swinging or rotating motion of a plurality of imaging detectors or detector heads.

In particular, a plurality of imaging detectors 102 are mounted to a gantry 104 and/or a patient support structure (not shown) (e.g., under a patient table 120), which may define a table support for a patient table 120. In the illustrated embodiment, the imaging detectors 102 are configured as a detector array 106 positioned around the subject 110 (e.g., a patient), as viewed in FIG. 1. The detector array 106 may be coupled directly to the gantry 104, or may be coupled via support members 112 thereto, to allow movement of the entire array 106 relative to the gantry 104 (e.g., rotational movement in the clockwise or counter-clockwise direction as viewed in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly. Thus, in the illustrated embodiment the detector array 106 is around the subject 110 and may allow linear movement of the detector units 114, such as towards or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112 and/or gantry 104, which in various embodiments allows the detector units 114 to move linearly towards and away from the support member 112, such as radially inward and outwards for positioning adjacent the subject 110. For example, as described herein, the detector units 114 may be controlled to move independently of each other towards or away from the subject 110, as well as capable of rotational, pivoting, or tilting movement in some embodiments.

Each of the imaging detectors 102 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors may be different sizes and/or shapes with respect to each other, such as square, rectangular, circular, or another shape. An actual field of view (FOV) of each of the imaging detectors 102 may be directly proportional to the size and shape of the respective imaging detector.

The gantry 104 may be formed with an aperture 118 (e.g., opening or bore) therethrough as illustrated. The patient table 120 is configured with a support mechanism, such as the patient support structure, to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H", and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc shaped and the support members 112 movable along the arc to position the detector units 114 at different locations along the gantry 104. In some embodiments, the detector units 114 may also be independently movable along the gantry 104.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110), image data specific for a larger FOV may be acquired more quickly.

Each of the imaging detectors 102 has a radiation detection face, which is directed towards the subject 110 or a region of interest within the subject 110. The radiation detection faces may be covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimators.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

A controller unit 130 may control the movement and positioning of the patient table 120, imaging detectors 102, gantry 104, and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow coordinated movement of the detector array 106.

The pivot controller 138 may control pivoting, rotating, or swinging movement of the detector units 114 at ends of the detector carriers 116, and/or the detector carrier 116. For example, one or more of the detector units 114 or detector carriers 116 may be rotated or swung about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 102, gantry 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector array 106, which as illustrated in FIG. 1 are in a protracted position towards the subject 110. Positioning may be accomplished manually by the operator and/or automatically, which may include using other images acquired before the current acquisition, such as by another imaging modality such as CT, MRI, X-ray, PET, or ultrasound. Additionally, the detector units 114 may be configured to acquire non-NM data, such as x-ray CT data.

After the imaging detectors 102, gantry 104, patient table 120, and/or collimators 122 are positioned, one or more images are acquired by one or more of the imaging detectors 102 being used, which may include pivoting or swinging motion of one or more of the detector units 114, which may pivot, rotate, or swing to different degrees or between different ranges of angles. The image data acquired by each imaging detector 102 may be combined and reconstructed into a composite image, which may comprise two-dimensional (2D) images, a three-dimensional (3D) volume, or a 3D volume over time (4D).

In one embodiment, the imaging detectors 102, gantry 104, patient table 120, and/or collimators 122 remain stationary after being initially positioned. In another embodiment, an effective field of view for one or more of the imaging detectors may be increased by movement such as pivoting, rotating, or swinging one or more of the imaging detectors 102, rotating the detector array 106 with the gantry 104, adjusting one or more of the collimators 122, or moving the patient table 120.

In various embodiments, a data acquisition system (DAS) 160 receives electrical signal data produced by the imaging detectors 102 and converts this data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the imaging system 100, or may be located remotely. Additionally, a user input device 166 may be provided to receive user inputs (e.g., control commands), as well as a display 168 for displaying images.

Additionally, a detector position controller 165 is also provided, which may be implemented in hardware, software, or a combination thereof. For example, as shown in FIG. 1, the detector position controller 165 may form part of or operate in connection with the processing unit 150. In some embodiments, the detector position controller 165 may be a module that operates to control the movement of the imaging detectors 102, including the detector units 114, such that coordinated or synchronized movement is provided as described herein. It should be noted that movement of a plurality of the imaging detectors 102 and/or detector units 114 may be performed at the same time (e.g., simultaneously or concurrently) or at different times (e.g., sequentially or step-wise, such as back and forth between two detector units 114). It also should be understood that when referring to a detector head, such a detector head may include one or multiple detector modules.

In operation, and as shown, for example, in FIG. 2, one embodiment includes the detector array 106 positioned (e.g., mounted) under the patient table 120. As can be seen, a plurality of detector units 114a, 114b are positioned in adjacent arrangement, for example, along one or more rows under the patient table 120 (it should be noted that only a single row of detector units is shown). The detector units in some embodiments are aligned along one or more axes generally perpendicular to the longitudinal axis of the patient table 120, which defines an examination axis (e.g., from head to toe of the subject 110). However, it should be appreciated that the detector units may be aligned in different configurations and orientations, which may be offset from each other, transverse to the longitudinal axis of the patient table 120 and/or parallel to the longitudinal axis of the patient table 120. The detector units illustrated in FIG. 2 may each be non-limiting examples of detector unit 114 of FIG. 1. Further, detector units 114a illustrated in FIG. 2 are arranged at an angle relative to a longitudinal axis of the detector units (which is perpendicular to a longitudinal axis of the patient table) and detector units 114b illustrated in FIG. 2 are arranged parallel to the longitudinal axis of the detector units.

As can be seen in the illustrated embodiment, each of the detector units 114a, 114b includes a housing 170, which are illustrated as circular. However, the housing 170 of the detector units 114a, 114b may have different shapes and sizes, for example, oval, other curved shapes, etc. The detector units 114a, 114b include within the housing 170 a detector support 172, which may be a frame or other support structure. A detector 174 is coupled to the detector support 172. For example, the detector 174 may include one or more CZT tiles or modules as described herein, which are connected to electronics 176 (e.g., output electronics to output detected events) therein. Additionally, the collimator 122 is mounted to a front detecting surface of the detector 174. Thus, the detector support 172 is sized and shaped, such as having a base and/or walls, to support and maintain the components of the detector unit 114a, 114b within the housing 170. For example, the components of the detector unit 114a, 114b are maintained within the housing 170 when the housing rotates, pivots, or swings as described in more detail herein. In the illustrated embodiment, the detector units 114a are shown in a rotated, pivoted, or swung position, while the detector units 114b are shown in a non-rotated, non-pivoted, or non-swung position. As can be seen, in the non-rotated, non-pivoted, or non-swung position, the detecting face of the detector is generally parallel to the patient support surface of the patient table 120, while in the rotated, pivoted, or swung position, the detecting face of the detector is not parallel to the patient support surface of the patient table 120. Various embodiments provide coordinated or synchronized movement of the detector units 114a, 114b, which allows the detector units 114a, 114b to be positioned or packed in closer alignment than in conventional systems. For example, in some embodiments, different detector units 114a, 114b, such as adjacent detector units 114 may move along different angular ranges, to a different angular position, and/or at different velocities.

It should be noted that the arrangement of detector units 114 in the detector array 106 may be provided in other portions of the NM imaging system 100, such as at positions along the gantry 104 or as part of the detector array 106. Also, it should be noted that in some embodiments, a housing 170 is not provided surrounding or encasing the components within the detector units 114.

As seen in FIG. 2, the housings 170 for detector units 114 are generally circular in shape and lie in close proximity to each other. As such, rotation of each detector unit 114 about its individual axis does not physically interfere with the adjacent detector units. The circular housings 170 allow for a small clearance in between each detector unit 114 to allow for complete rotation of each detector unit during operation of the imaging system 100.

Figure 3:
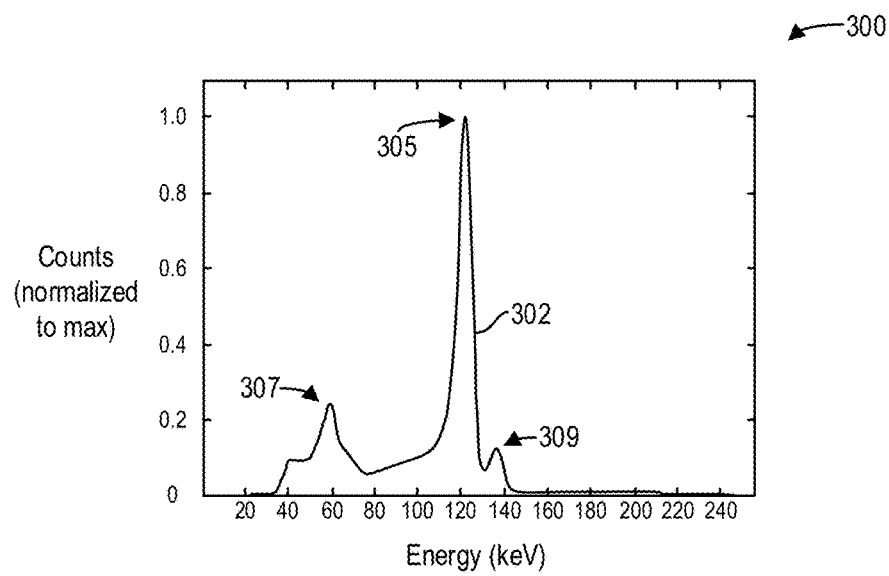
FIG. 3 shows a graph illustrating an energy spectrum of an example calibration source in accordance with an embodiment.

FIG. 3 shows a graph 300 illustrating an energy spectrum 302 of an example calibration source in accordance with an embodiment. The graph 300 illustrates the energy spectrum 302 of the calibration source in terms of photon counts as a function of energy (measured in kiloelectronvolts).

As discussed further herein, a calibration source for an NM imaging system may include a radioisotope and an x-ray fluorescence source. The radioisotope emits gamma radiation which may be detected by the gamma cameras of the NM imaging system. The gamma radiation emitted by the radioisotope also stimulates the x-ray fluorescence source to emit x-rays which may also be detected by the gamma cameras of the NM imaging system.

Thus, as depicted, the energy spectrum 302 includes an energy peak 305 corresponding to the gamma radiation emitted by the radioisotope, as well as an energy peak 307 corresponding to the x-ray radiation emitted by the x-ray fluorescence source. Since the x-ray fluorescence is stimulated by the gamma radiation, the counts of the energy peak 307 are less than the counts of the energy peak 305. In other words, fewer photons are detected from the x-ray fluorescence source than are detected from the radioisotope. Further, the use of a radioisotope in conjunction with an x-ray fluorescence source provides distinct energy peaks for two point energy calibration, whereas the use of two radioisotopes in a calibration source would provide energy peaks that are closer together and possibly more difficult to distinguish.

In the particular example depicted, the radioisotope of the calibration source comprises cobalt-57, while the x-ray fluorescence source of the calibration source comprises tungsten. Consequently, the energy peak 305 corresponds to an energy level of 122 kiloelectronvolts (keV), while the energy peak 307 corresponds to an energy level of 58.8 keV. The energy spectrum 302 further includes a third energy peak 309 corresponding to a secondary energy peak of cobalt-57, with an energy level of 136 keV; the energy peak 309 may be too small and too close to the energy peak 307 for two-point energy calibration. Since the energy spectrum 302 of the calibration source is known, a gamma camera or detector of an NM imaging system can be calibrated by measuring the energy spectrum of the calibration source with the gamma camera, and adjusting the gain and offset of the gamma camera based on a comparison of the known energy spectrum 302 to the energy spectrum measured by the gamma camera.

The calibration source may comprise cobalt-57 due to the commercial availability and more affordable price of cobalt-57 in comparison to other radioactive sources. Further advantageously, the radiation energy of cobalt-57 is close to the 140 keV energy peak of the common radiopharmaceutical technetium-99m, and so careful calibration in this energy region is desirable. Even further, cobalt-57 may be easily shielded in a relatively thin sheath when not in use. Further still, the half-life of cobalt-57 (which is approximately a year) means that the calibration source does not need replaced often.

The fluorescence source may comprise tungsten due to the non-toxicity of tungsten (especially in comparison with lead). Further, the x-ray energy peak of tungsten is separated enough from the cobalt-57 emission and is high enough to be easily detected by the detector.

It should be noted that the term energy peak as used herein generally refers to the main energy emission from the decay of a radiopharmaceutical injected within a patient and which is calibrated by a corresponding isotope using the calibration source. Additionally, the term energy window as used herein generally refers to the energy used for image reconstruction, which includes the photons with measured energy that fall within the energy range (defined by a width of an energy window) around the energy of the spectrum peak, which corresponds to the energy of the radioisotope as measured by a gamma camera or detector.

FIG. 4 shows multiple views of an example calibration source 400 in accordance with an embodiment. The multiple views include an axial cross-sectional view 405 and a coronal cross-sectional view 410 of the calibration source 400. The calibration source 400 includes a radioisotope line source 412 and an x-ray fluorescence source 414.

As depicted in both views 405 and 410, the line source 412 comprises a cylinder with a radius, and the fluorescence source 414 comprises a cuboidal slab with a width greater than the radius of the line source 412. It should be noted that fluorescence source 414 may take other forms and shapes, for example such as a trough, or may have an "L" shaped cross section. As depicted in view 410, the length of the line source 412 and the length of the fluorescence source 414 may be substantially the same.

In one example, the line source 412 may comprise a radioisotope such as cobalt-57 while the fluorescence source 414 may comprise tungsten. The energy spectrum of the calibration source 400 may therefore resemble the energy spectrum 302 described hereinabove with regard to FIG. 3.

It should be noted that different isotopes and materials may be used to form the calibration source 400. For example, the isotope line source 412 may be configured as a line source filled with technetium-99m providing an energy peak at 140.5 keV instead of the 122 keV energy peak of cobalt-57. Also, different cobalt isotopes may be used, including but not limited to cobalt-60. Additionally, the fluorescence source 414 may be coated with other materials to provide additional or different energy peaks. Additionally, materials other than tungsten may be used to form the fluorescence source 414. As illustrative and non-limiting examples, the fluorescence source 414 may be formed from bismuth, lead, tantalum, barium, and tin.

In some examples, the fluorescence source 414 may be formed from a multi-layer structure, for example, comprising a bi-layer of tungsten and lead. In this example multi-layer structure, the fluorescence from the tungsten creates an energy peak at 59 keV and the fluorescence from the lead creates energy peaks at 75 keV and 85 keV.

The calibration source 400 may be sized based on the size of an NM imaging system. For example, in order to provide sufficient radiation to all detector pixels, the length of the calibration source 400 may be equal to or greater than the length of a detector of the imaging system.

As an illustrative example, FIG. 5 shows a block diagram 500 illustrating relative sizes of a calibration source 505 and a detector 510 in accordance with an embodiment. The calibration source 505, which may comprise the calibration source 400 described hereinabove, has a length 507 in the longitudinal (also referred to as the axial) direction 515 of the NM imaging system (i.e., into the bore of the imaging gantry). Meanwhile, detector 510 has a length 512 in the longitudinal direction 515. As depicted, the length 507 of the calibration source 505 is greater than the length 512 of the detector 510 in the longitudinal direction 515, though it should be appreciated that the length 507 may be at least equal to the length 512 of the detector 510. In this way, the calibration source 505 can be used to calibrate the detector 510 without repositioning the calibration source with respect to the detector 510 during the calibration.

It should be appreciated that the length 512 of the detector 510 indicates the active imaging area or field-of-view (FOV) of the detector 510, determined by the size of the active detector face and the collimator fixed thereto, whereas the full length of the detector 510 including shielding and other structural components may be longer than the length 512. As an example, the FOV of a detector may be 4×28 centimeters, and so the length 507 of the calibration source 505 may be at least 28 centimeters in such an example.

FIG. 6 shows a block diagram illustrating an example calibration source 605 positioned within a NM imaging system 600 in accordance with an embodiment. The calibration source 605 may comprise the calibration source 400 described herein above with regard to FIG. 4, and thus may comprise a cylindrical radioisotope line source 607 and a cuboidal x-ray fluorescence source 608 as depicted.

The NM imaging system 600 includes a plurality of gamma cameras or detector heads 610, each detector head 610 coupled to a corresponding detector carrier or arm 612 which are in turn coupled to the gantry 615 of the NM imaging system 600. Specifically, the gantry 615 includes a stator 616 and a rotor 617; the detector arms 612 are coupled to the rotor 617 of the gantry 615 such that rotation of the rotor 617 rotates the position of the plurality of detector heads 610 with respect to the stator 616 and the calibration source 605.

The calibration source 605 is positioned in the imaging bore 618 of the gantry 615. As an example, the calibration source 605 may be positioned on a patient table (not shown), such as the patient table 120 described hereinabove with regard to FIG. 1. The line source 607 of the calibration source 605—which may comprise the line source 412 and the calibration source 400, respectively, described hereinabove with regard to FIG. 4—emits gamma rays in all directions; gamma rays emitted in the direction of the fluorescence source 608 are absorbed by the fluorescence source 608 which in turn emits x-rays. The detector heads 610 detect gamma rays emitted by the line source 607 as well as x-rays emitted by the fluorescence source 608.

Since the fluorescence source 608 absorbs some of the gamma rays emitted by the line source 607, and further due to the physical configuration of the calibration source 605, the calibration source 605 comprises an anisotropic source. In other words, the calibration source 605 as a whole does not emit equal amounts of gamma rays and x-rays in all directions. Consequently, not all of the detector heads 610 may detect sufficient numbers of gamma rays or x-rays to perform calibration. For example, detector heads 610a may receive sufficient radiation (including both gamma rays and x-rays) from the calibration source 605 for calibration, due to the position of detector heads 610a with respect to the calibration source 605. Detector heads 610b may receive some radiation (i.e., gamma rays and x-rays) from the calibration source 605, but due to the position of the detector heads 610b, the amount of radiation may be inadequate for calibration. The fluorescence source 608 may shield the gamma rays emitted from the line source 607 such that the gamma rays cannot reach the detector heads 610c, and so the detector heads 610c may not receive sufficient radiation for calibration.

Therefore, in some examples, the plurality of detector heads 610 may be rotated about the calibration source 605 such that each detector head 610 may acquire sufficient amounts of radiation from the calibration source 605 to perform a calibration. In some examples, the rotation of the detector heads 610 in a clockwise or counter-clockwise direction, which is performed by rotating the rotor 617 of the gantry 615, may be performed sequentially. For example, the three detector heads 610a may be positioned above the calibration source 605 and controlled to detect gamma rays and x-rays emitted by the calibration source 605 for a threshold amount of time or until a threshold number of photon counts is reached. The gantry 615 may then rotate the plurality of detector heads 610 in a clockwise or counter-clockwise direction until three additional detector heads 610 reach the depicted position of detector heads 610a above the calibration source 605. In the depicted example, the NM imaging system 600 includes twelve detector heads 610; if the calibration source 605 is scanned with three detector heads 610 at a time, the plurality of detector heads 610 may be rotated three times to allow each detector head 610 to scan the calibration source 605. It should be appreciated that the number of detector heads 610 and the number of rotations is exemplary and illustrative. In other examples, the rotation of the detector heads 610 may be continuous instead of discrete and sequential.

Further, during an acquisition, a detector head 610 may be pivoted, swung, or rotated as described hereinabove with regard to FIGS. 1-2 such that the calibration source 605 is within the field-of-view of each pixel of the detector head 610 during the acquisition.

FIG. 7 shows a diagram illustrating example geometry 700 of a detector head 701 while pivoting with respect to a calibration source 705 in accordance with an embodiment. The face 710 of the detector 701 may be oriented such that the incidence of photons emitted by the calibration source 705 is normal to the face 710 in the center of the face 710. During an acquisition of photons from the calibration source 705 by the detector 701, the detector head 701 may be rotated about a central axis of rotation 721 such that the face 710 sweeps out an angle 722, also depicted as the angle φ.

Distance 732 is greater than distance 734, and so the point spread function (PSF) of the detector oriented with φ=0 is greater than the PSF of the detector oriented with φ≠0. Further, the intensity of incident radiation on the un-pivoted detector face 710 is less than the intensity of incident radiation on the pivoted detector face, since intensity is inversely proportional to the distance squared. Therefore, as the detector sweeps from an orientation with φ≠0 to an orientation with φ=0, the PSF increases while the intensity decreases, which produces a variation in the acquisition. This variation is depicted in the graph 750 which illustrates an example profile 752 of photon counts as a function of pixel position measured while the detector was pivoting at a constant rate. As depicted, the intensity initially decreases as φ increases away from 0 and then increases as the angle continues to increase. Thus, there is a need for geometrical correction, as the photon counts and energy measurements recorded by each pixel may be slightly distorted due to the pivoting of the detector.

Figure 8:
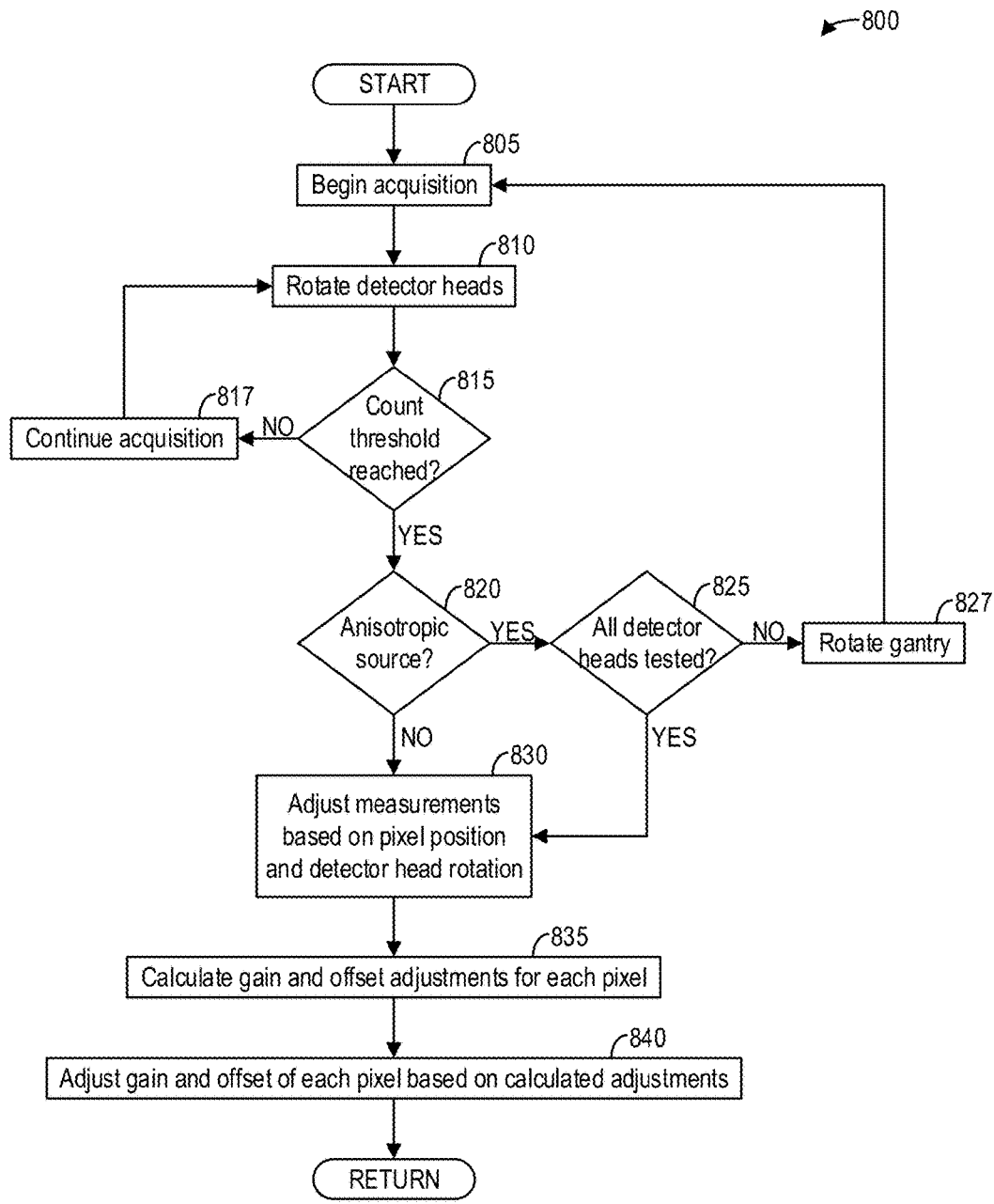
FIG. 8 shows a high-level flow chart illustrating an example method for calibrating a NM imaging system in accordance with an embodiment.

FIG. 8 shows a high-level flow chart illustrating an example method 800 for calibrating a NM imaging system in accordance with an embodiment. In particular, method 800 relates to calibrating the gamma cameras of a NM imaging system with a calibration source comprising a single radioisotope and an x-ray fluorescence source. Method 800 will be described herein with reference to the system and components depicted in FIGS. 1-2, though it should be understood that the method may be applied to other systems without departing from the scope of this disclosure. Method 800 may be carried out by processing unit 150, and may be stored as executable instructions in non-transitory memory of the processing unit 150.

Method 800 begins at 805. At 805, method 800 begins the acquisition of photons emitted by a calibration source positioned within the imaging system. During the acquisition, at 810, method 800 rotates or pivots the detector heads acquiring the photons such that all pixels of the detector heads are exposed to the radiation.

At 815, method 800 determines if a count threshold is reached. The count threshold may comprise a threshold number of photons detected by at least a portion of the pixels of a detector. Alternatively, in some examples, a time threshold may be utilized instead of a count threshold. For example, the method may perform the acquisition for a predetermined amount of time. If the count threshold (or alternatively, the time threshold) is not reached ("NO"), method 800 proceeds to 817 wherein the method continues the acquisition. Method 800 then returns to 810 to continue pivoting the detector heads.

Referring again to 815, if the count threshold is reached ("YES"), method 800 proceeds to 820. At 820, method 800 determines if the calibration source is an anisotropic source. An anisotropic source may comprise, for example, the calibration source 400 described herein above, wherein the fluorescence source shields gamma rays from the line source from reaching one or more detectors. In some examples, the calibration source may be isotropic, such that the gamma rays emitted by the line source are capable of reaching all detectors of the imaging system. Example isotropic calibration sources are described further herein with regard to FIGS. 9-13.

If the calibration source is not anisotropic ("NO"), method 800 proceeds to 830. However, if the calibration source is anisotropic ("YES"), method 800 proceeds to 825. At 825, method 800 determines if all detector heads are tested. If not all detector heads are detected ("NO"), method 800 proceeds to 827. At 827, method 800 rotates the gantry such that the emissions of the calibration source are within the field-of-view of the untested detector heads. Method 800 then returns to 805 to begin an acquisition with the untested detector heads. In this way, for an anisotropic calibration source such as the calibration source 400 described hereinabove, the method rotates the detector heads about the calibration source and repeats the acquisition until all detector heads acquire enough data to calibrate each detector head. Alternatively, or if the gantry has a limited rotation range, the calibration source 605 (e.g. line source 607 with fluorescence source 608) may be rotated to face another set of detectors 610b or 610c.

Referring again to 825, once all detector heads are tested ("YES"), method 800 proceeds to 830. At 830, method 800 applies a geometric correction to the acquired data by adjusting the measurements based on the pixel position and detector head rotation.

At 835, method 800 calculates gain and offset adjustments for each pixel of each detector to achieve uniform energy and sensitivity response across the detectors. The gain and offset adjustments are based on the energy spectrum of the multi-peak calibration source, which provides at least two distinct energy peaks. More specifically, the gain and offset adjustments are calculated such that the measured energy spectrum of the calibration source corresponds to the known energy spectrum of the calibration source. Continuing at 840, method 800 adjusts the gain and offset of each pixel based on the calculated adjustments. Method 800 then ends.

Figure 9:
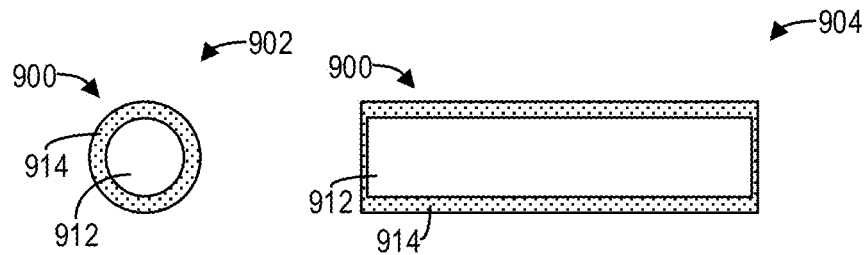
FIG. 9 shows different views of an example isotropic calibration source in accordance with an embodiment.

FIG. 9 shows different views of an example isotropic calibration source 900 in accordance with an embodiment. Specifically, the different views include an axial cross-sectional view 902 of the calibration source 900 and a coronal cross-sectional view 904 of the calibration source 900. The calibration source 900 comprises a cylindrical radioactive line source 912, which may be filled with a radioisotope such as cobalt-57 or another suitable radioisotope. The calibration source 900 further comprises a fluorescence source 914 formed as a cylindrical sheath that encloses the line source 912. As an example, the fluorescence source 914 may be formed from epoxy resin mixed with tungsten powder. The concentration of tungsten powder in the fluorescence source 914 may be great enough to enable x-ray fluorescence without completely shielding the line source 912.

Figure 10:
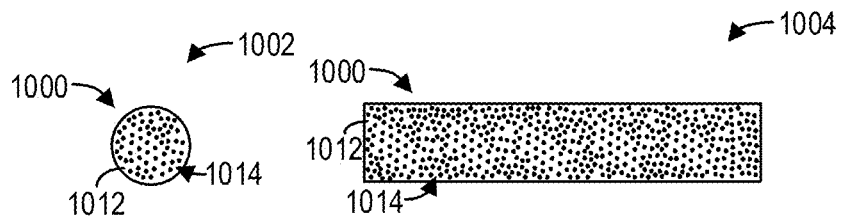
FIG. 10 shows different views of another example isotropic calibration source in accordance with an embodiment.

FIG. 10 shows different views of another example isotropic calibration source 1000 in accordance with an embodiment. Specifically, the different views include an axial cross-sectional view 1002 of the calibration source 1000 and a coronal cross-sectional view 1004 of the calibration source 1000. The calibration source 1000 includes a cylindrical radioactive line source 1012 with a fluorescence source 1014 integrally formed therein. For example, the calibration source 1000 may comprise a cylinder filled with a mixture of cobalt-57 (or another suitable radioisotope) and a fine powder of tungsten (or another suitable fluorescence source). In this way, both gamma rays and x-rays may be emitted from the cylindrical line source 1000.

As a specific example, the radioactive material, such as cobalt, may be mixed with tungsten powder and epoxy resin, and poured into a stainless steel tube. The tube is then laser welded at the ends to seal the cobalt-tungsten mixture inside of the tube.

Figure 11:
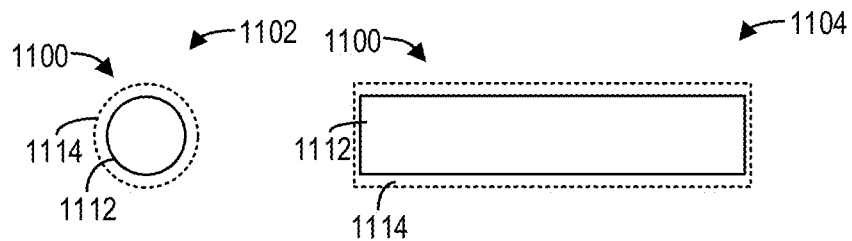
FIG. 11 shows different views of yet another example isotropic calibration source in accordance with an embodiment.

FIG. 11 shows different views of yet another example isotropic calibration source 1100 in accordance with an embodiment. The different views include an axial cross-sectional view 1102 and a coronal cross-sectional view 1104 of the calibration source 1100. The calibration source 1100 includes a cylindrical line source 1112, which may comprise, similar to the line sources described hereinabove, a radioisotope such as cobalt-57. The calibration source 1100 further includes a fluorescence source 1114. The fluorescence source 1114 may comprise a thin foil made from tungsten powder and formed into a sheath to enclose the cylindrical line source 1112.

Figure 12:
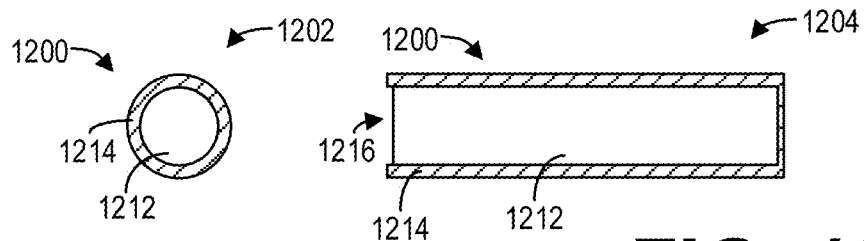
FIG. 12 shows different views of another example isotropic calibration source in accordance with an embodiment.

FIG. 12 shows different views of another example isotropic calibration source 1200 in accordance with an embodiment. The different views include an axial cross-sectional view 1202 and a coronal cross-sectional view 1204 of the calibration source 1200. The calibration source 1200 includes a cylindrical line source 1212 formed from a radioisotope such as cobalt-57. The calibration source 1200 further includes a fluorescence source 1214 formed as a sheath that encloses the cylindrical line source 1212. In this example, the fluorescence source 1214 comprises a wire formed from, as a non-limiting example, tungsten, which is wrapped around the line source 1212. In some examples, the fluorescence source 1214 may comprise a tube with tungsten wire wrapped around the tube.

In the depicted example, the fluorescence source 1214 includes an opening 1216 at one end of the calibration source 1200 that exposes the line source 1212. It should be appreciated that in other embodiments wherein the fluorescence source comprises a sheath, such as the calibration source 900 or the calibration source 1100, the sheath may include an opening such as opening 1216 to provide access to the line source enclosed within the sheath.

It should be appreciated that in each of the examples depicted in FIGS. 9-12, some of the fluorescence source (e.g., tungsten) may absorb more of the gamma radiation (e.g., from the cobalt line source) and consequently emit more x-ray radiation. As a result, the tungsten and cobalt energy peaks may be at least partially normalized in comparison to peaks of FIG. 3. It should be appreciated that in each of the examples depicted in FIGS. 9-12, radiation arrives to all the detectors (in contrast to the anisotropic radiation of sources 400 and 605 seen in FIGS. 4 and 6), and thus, all the detectors may be calibrated at the same time. The result is a faster and/or more convenient calibration process. In the method of FIG. 8, steps 825 and 827 may therefore be unnecessary.

Figure 13:
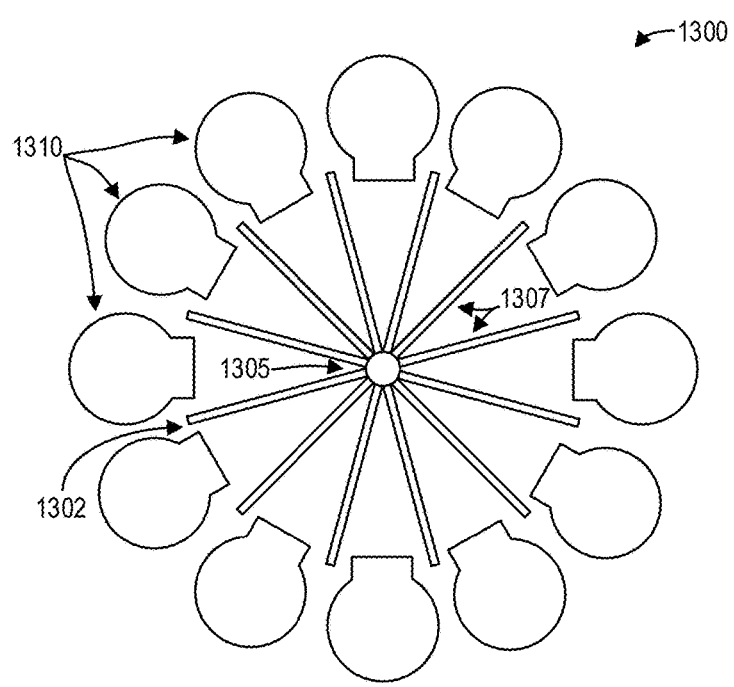
FIG. 13 shows a diagram illustrating yet another example calibration source in accordance with an embodiment.

FIG. 13 shows a diagram illustrating an example configuration 1300 for an example calibration source 1302 in accordance with an embodiment. Similar to the examples described herein above, the calibration source 1302 includes a cylindrical line source 1305. As depicted, the calibration source 1302 further includes a fluorescence source 1307 comprising a plurality of planar foils extending radially from the line source 1305. The planar foils may comprise sheets of tungsten. In some examples, the tungsten foils 1307 may at least partially towards the plurality of detector heads 1310. Similarly to the examples depicted in FIGS. 9-12, in the example depicted in FIG. 13, the radiation also arrives to all the detectors.

A technical effect of the disclosure is the calibration of detector heads using a single calibration source. Another technical effect of the disclosure is the pivoting of detector heads while scanning a calibration source. Yet another technical effect of the disclosure is a uniform energy and sensitivity response across detector heads or output channels.

In one embodiment, a method comprises: detecting, with a plurality of detectors, photons emitted by a calibration source comprising a radioactive line source and a fluorescence source, while pivoting one or more detectors of the plurality of detectors; and calibrating, with a processor communicatively coupled to the plurality of detectors, each detector of the plurality of detectors based on energy measurements of the detected photons.

In a first example of the method, the method further comprises applying a geometrical correction to the energy measurements based on the pivoting of the one or more detectors. In a second example of the method optionally including the first example, applying the geometrical correction to the energy measurements comprises adjusting, for a pixel of the one or more detectors, photon counts based on a position of the pixel. In a third example of the method optionally including one or more of the first and second examples, calibrating each detector comprises adjusting a gain and an offset of each detector to account for differences between the energy measurements of the detected photons and a known energy spectrum of the calibration source. In a fourth example of the method optionally including one or more of the first through third examples, the plurality of detectors are coupled to a gantry, and further comprising, during the detecting of the photons, rotating the gantry. In a fifth example of the method optionally including one or more of the first through fourth examples, the radioactive line source comprises a cylinder filled with a single isotope. In a sixth example of the method optionally including one or more of the first through fifth examples, the fluorescence source comprises a sheath, and wherein the radioactive line source is positioned within the sheath. In a seventh example of the method optionally including one or more of the first through sixth examples, the sheath comprises one of a thin foil or a wire. In an eighth example of the method optionally including one or more of the first through seventh examples, the fluorescence source comprises a plurality of planar foils extending radially from the radioactive line source. In a ninth example of the method optionally including one or more of the first through eighth examples, the fluorescence source comprises a slab fixedly attached to the radioactive line source.

In another embodiment, a system comprises: a gantry defining a bore; a calibration source comprising a radioactive line source and a fluorescence source, the calibration source positioned within the bore; a plurality of detectors coupled to the gantry and configured to detect radiation from the calibration source; and a processor communicatively coupled to the plurality of detectors and configured with instructions in non-transitory memory that when executed cause the processor to: detect, with the plurality of detectors, photons emitted by the calibration source while pivoting one or more detectors of the plurality of detectors; and adjust a gain and offset of at least one detector of the plurality of detectors based on an energy spectrum of the detected photons.

In a first example of the system, the calibration source is anisotropic, and the processor is further configured with instructions in the non-transitory memory that when executed cause the processor to rotate the gantry to reposition the plurality of detectors relative to the calibration source. In a second example of the system optionally including the first example, the processor is further configured with instructions in the non-transitory memory that when executed cause the processor to apply a geometrical correction to the energy spectrum based on the pivoting of the one or more detectors. In a third example of the system optionally including one or more of the first and second examples, the radioactive line source comprises an isotope of cobalt and the fluorescence source comprises tungsten. In a fourth example of the system optionally including one or more of the first through third examples, the fluorescence source comprises a sheath that encloses the radioactive line source. In a fifth example of the system optionally including one or more of the first through fourth examples, the fluorescence source is integrally formed with the radioactive line source.

In yet another embodiment, a calibration source for a nuclear medicine (NM) imaging system comprises: a radioactive line source shaped as a cylinder with a length equal to or greater than a length of a detector of the NM imaging system, the radioactive line source comprising a radioisotope with an energy spectrum including a first energy peak; and a fluorescence source, wherein an energy spectrum of the fluorescence source includes a second energy peak, the second energy peak distinguishable from the first energy peak by the detector.

In a first example of the calibration source, the fluorescence source comprises a tungsten powder distributed throughout the radioactive line source. In a second example of the calibration source optionally including the first example, the fluorescence source comprises a tungsten foil or a tungsten wire forming a sheath around the radioactive line source. In a third example of the calibration source optionally including one or more of the first and second examples, the fluorescence source comprises a tungsten slab, and the radioactive line source is fixedly attached to and positioned in the center of the tungsten slab.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   detecting, with a plurality of detectors, photons emitted by a calibration source comprising a radioactive line source and a fluorescence source, while pivoting one or more detectors of the plurality of detectors;
   applying a geometrical correction to energy measurements of the detected photons, wherein applying the geometrical correction includes increasing photon counts of at least one pixel of the one or more detectors according to the pivoting of the one or more detectors; and
   calibrating, with a processor communicatively coupled to the plurality of detectors, each detector of the plurality of detectors based on the geometrically-corrected energy measurements of the detected photons.

2. The method of claim 1, further comprising applying the geometrical correction account for distortions in the photon counts and the energy measurements caused by the pivoting of the one or more detectors.

3. The method of claim 1, wherein applying the geometrical correction to the energy measurements comprises adjusting, for a pixel of the one or more detectors, photon counts recorded by the pixel based on a position of the pixel and the pivoting of the one or more detectors relative to the calibration source.

4. The method of claim 1, wherein calibrating each detector comprises adjusting a gain and an offset of each detector to account for differences between the energy measurements of the detected photons and a known energy spectrum of the calibration source.

5. The method of claim 1, wherein the plurality of detectors is coupled to a gantry, and further comprising, during the detecting of the photons, rotating the gantry.

6. The method of claim 1, wherein the radioactive line source comprises a cylinder filled with a single isotope.

7. The method of claim 6, wherein the fluorescence source comprises a sheath, and wherein the radioactive line source is positioned within the sheath.

8. The method of claim 7, wherein the sheath comprises one of a thin foil or a wire.

9. The method of claim 6, wherein the fluorescence source comprises a plurality of planar foils extending radially from the radioactive line source.

10. The method of claim 6, wherein the fluorescence source comprises a slab fixedly attached to the radioactive line source.

11. A system, comprising:
a gantry defining a bore;
a calibration source comprising a radioactive line source and a fluorescence source, the calibration source positioned within the bore;
a plurality of detectors coupled to the gantry and configured to detect radiation from the calibration source; and
a processor communicatively coupled to the plurality of detectors and configured with instructions in non-transitory memory that, when executed, cause the processor to:
detect, with the plurality of detectors, photons emitted by the calibration source while pivoting one or more detectors of the plurality of detectors;
apply a geometrical correction to an energy spectrum of the detected photons by adjusting photon counts and energy measurements recorded by pixels of the one or more detectors according to the pivoting of the one or more detectors, wherein adjusting the photon counts and the energy measurements for a pixel includes increasing or decreasing the photon counts and the energy measurements according to a position of the pixel; and
adjust a gain and an offset of at least one detector of the plurality of detectors based on the geometrically-corrected energy spectrum of the detected photons.

12. The system of claim 11, wherein the calibration source is anisotropic, and wherein the processor is further configured with instructions in the non-transitory memory that, when executed, cause the processor to rotate the gantry to reposition the plurality of detectors relative to the calibration source.

13. The system of claim 11, wherein the calibration source is isotropic.

14. The system of claim 11, wherein the radioactive line source comprises an isotope of cobalt and the fluorescence source comprises tungsten.

15. The system of claim 13, wherein the fluorescence source comprises a sheath that encloses the radioactive line source.

16. The system of claim 13, wherein the fluorescence source is integrally formed with the radioactive line source.

17. A system, comprising:
a detector of a nuclear medicine (NM) imaging system with a length along an axial direction of the NM imaging system; and
a calibration source positioned within the NM imaging system for calibrating the detector, the calibration source comprising:
a radioactive line source shaped as a cylinder with a length equal to or greater than the length of the detector of the NM imaging system, the radioactive line source comprising a radioisotope with an energy spectrum including a first energy peak; and
a fluorescence source, wherein an energy spectrum of the fluorescence source includes a second energy peak, the second energy peak distinguishable from the first energy peak by the detector.

18. The system of claim 17, wherein the fluorescence source comprises a tungsten powder distributed throughout the radioactive line source.

19. The system of claim 17, wherein the fluorescence source comprises a tungsten foil or a tungsten wire forming a sheath around the radioactive line source.

20. The system of claim 17, wherein the fluorescence source comprises a tungsten slab, and the radioactive line source is fixedly attached to, and positioned in the center of, the tungsten slab.

* * * * *